United States Patent [19]

Kataoka et al.

[11] Patent Number: 4,575,570

[45] Date of Patent: Mar. 11, 1986

[54] PROCESS FOR PRODUCING ALPHA, BETA-UNSATURATED KETONES

[75] Inventors: Hideaki Kataoka, Yokohama; Toshiro Yamada, Fujisawa; Kuniaki Goto, Tokyo; Jiro Tsuji, Kamakura, all of Japan

[73] Assignee: Nippon Zeon Co., Ltd., Tokyo, Japan

[21] Appl. No.: 636,379

[22] Filed: Jul. 31, 1984

[30] Foreign Application Priority Data

Aug. 2, 1983 [JP] Japan ............................ 58-141488
Aug. 2, 1983 [JP] Japan ............................ 58-141489

[51] Int. Cl.$^4$ ............................................. C07C 45/65
[52] U.S. Cl. ..................................... 568/346; 568/388; 560/174; 560/121; 560/126
[58] Field of Search ............... 568/388, 347, 397, 346; 560/121, 174, 126

[56] References Cited

U.S. PATENT DOCUMENTS 4,496,766  1/1985  Tsuji et al. ........................ 568/388

OTHER PUBLICATIONS

Tsuda et al., J.A.C.S., vol. 102, pp. 6381-6384 (1980).
Isao Shimizu, et al., "Palladium-Catalyzed Decarboxylation-Dehydration of Allyl Beta-Keto Carboxylates and Allyl Enol Carbonates as a Novel Synthetic Method for Alpha-Substituted Alpha Beta-/Unsaturated Ketones,"—J. of Chem. Soc., 104 (1982), pp. 5844-5846.

Primary Examiner—James H. Reamer
Attorney, Agent, or Firm—Sherman and Shalloway

[57] ABSTRACT

A process for producing alpha,beta-unsaturated ketones represented by the following general formula

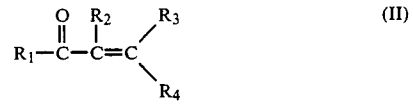

wherein $R_1$ represents a hydrocarbon radical, $R_2$ represents an organic radical bonded through a carbon-carbon bond, $R_3$ and $R_4$ represent a hydrogen atom or a hydrocarbon radical, and $R_1$, $R_2$, $R_3$ and $R_4$ may be straight-chained or form a ring in arbitrary combinations, which comprises contacting an alpha-disubstituted-beta-keto acid ester represented by the general formula

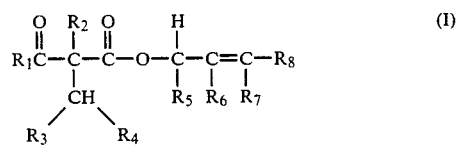

wherein $R_1$, $R_2$, $R_3$ and $R_4$ are as defined, and $R_5$, $R_6$, $R_7$ and $R_8$ represent a hydrogen atom or a hydrocarbon radical, with a catalyst consisting essentially of (a) a compound of a platinum-group metal and optionally (b) a monodentate ligand (b).

21 Claims, No Drawings

PROCESS FOR PRODUCING ALPHA, BETA-UNSATURATED KETONES

BACKGROUND OF THE INVENTION

This invention relates to a novel process for producing alpha,beta-unsaturated ketones. More specifically, it relates to a process for producing alpha,beta-unsaturated ketones starting from alpha-disubstituted-beta-keto acid esters.

Unsaturated ketones such as cyclopentenone derivatives, cyclohexenone derivatives and cyclododecenone derivatives are useful chemical substances in the fields of perfumes, medicines and chemicals.

Recently, a new process for synthesizing such an unsaturated ketone was reported which comprises treating an alpha-disubstituted-beta-keto acid ester with a catalyst consisting essentially of a palladium compound and an alpha,omega-alkylenedi(disubstituted)phosphine (Journal of Chemical Society, 1982, 104, 5844–5846). This document states that the above reaction is a specific reaction which takes place only when the alpha,omega-alkylenedi(disubstituted)phosphine is used as a ligand, and the use of an ordinary ligand such as triphenyl phosphine leads to a different reaction.

Accordingly, in such a prior technique, the ligands that can be used are limited to expensive compounds having a special structure. Moreover, this technique does not prove to be entirely satisfactory in regard to the activity of the catalyst, the selectivity of the reaction and the stability of the catalyst in the reaction system.

SUMMARY OF THE INVENTION

We made extensive investigations in order to remove the defects of the prior technique, and have found that this reaction does not always require the alpha,omega-alkylenedi(disubstituted)phosphine regarded as an essential catalyst ingredient in the above report; that a monodentate ligand such as triphenyl phosphine when used in a specific proportion is more effective than the alpha,omega-alkylenedi(disubstituted)phosphine; and that when the reaction is carried out in the presence of a certain compound, the activity and stability of the catalyst are further improved.

According to this invention, there is provided a process for producing an alpha,beta-unsaturated ketone represented by the following general formula [II], which comprises contacting an alpha-disubstituted-beta-keto acid ester represented by the following general formula [I] optionally in the presence of an allyl compound with a catalyst consisting essentially of (a) a compound of a platinum-group metal and as required, (b) a monodendate ligand in an amount of not more than 2.5 moles per mole of said compound (a).

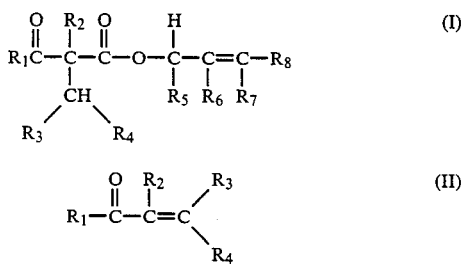

In the above formulae, $R_1$ represents a hydrocarbon radical, $R_2$ represents an organic radical bonded through a carbon-carbon bond, $R_3$, $R_4$, $R_5$, $R_6$, $R_7$ and $R_8$ represent a hydrogen atom or a hydrocarbon radical, and $R_1$, $R_2$, $R_3$ and $R_4$ may be straight-chained or form a ring in arbitrary combinations.

DETAILED DESCRIPTION OF THE INVENTION

In the process of this invention, the allylic ester of the alpha-disubstituted-beta-keto acid represented by general formula [I] is used as a starting material. In the formula, $R_1$ is preferably an alkyl radical such as a methyl, ethyl, propyl, butyl or pentyl radical, or an alkylene radical which forms a ring such as a cyclopentane, cyclohexane or cyclododecane ring together with $R_2$, $R_3$ or $R_4$. $R_2$ is preferably the same alkyl or alkylene radical as $R_1$, or an organic radical having a polar radical such as an alkoxycarbonyl, alkenoxycarbonyl, alkoxyalkyl or alkoxycarbonylalkyl radical and being bonded to the adjacent carbon atom through a carbon-carbon bond. $R_3$ and $R_4$ are preferably hydrogen or the same alkyl or alkylene radical as $R_1$. $R_5$, $R_6$, $R_7$ and $R_8$ are preferably hydrogen or alkyl radicals. $R_1$, $R_2$, $R_3$ and $R_4$ may form a ring in arbitrary combinations.

Specific examples of the compound [I] include esters formed between alpha-disubstituted-beta-keto acids such as 1-alkyl-2-oxocyclopentanecarboxylic acids, 1-alkenyl-2-oxocyclopentanecarboxylic acids, 1-alkynyl-2-oxocyclopentanecarboxylic acids, 1-alkyl-2-oxocyclohexanecarboxylic acids, 1-alkenyl-2-oxocyclohexanecarboxylic acids, 1-alkoxycarbonylalkyl-2-oxocyclohexanecarboxylic acids, 1-alkenoxycarbonyl-2-oxocyclohexanecarboxylic acids, 1-alkoxyalkyl-2-oxocyclohexanecarboxylic acids, 1-alkyl-2-oxocyclododecanecarboxylic acid, 1-acetyl-1-cyclopentanecarboxylic acid, alpha-dialkylacetoacetic acids and alpha-dialkyl-beta-oxononanoic acids and allylic alcohols such as allyl alcohol, methallyl alcohol, crotyl alcohol, 2-pentenyl alcohol and 2-ethyl-2-butenol. The keto acids preferably have not more than 20 carbon atoms, and the allylic alcohols preferably have not more than 6 carbon atoms.

The compounds of formula [I] may be synthesized in a customary manner. For example, allyl 1-pentyl-2-oxocyclopentanecarboxylate can be synthesized by cyclizing diallyl adipate to allyl 2-oxocyclopentanecarboxylate by Dieckmann condensation, and reacting the product with n-pentyl bromide in the presence of potassium carbonate, or by reacting 2-pentyl cyclopentanone with allyl chloroformate.

The reaction in the process of this invention is catalyzed by a catalyst composed of (a) a compound of a platinum-group metal, or a catalyst composed of (a) a compound of a platinum-group metal and (b) a monodentate ligand.

The compound (a) of a platinum-group metal used is a salt or complex of palladium, platinum, rhodium, iridium or ruthenium. Specific examples include tris(dibenzylideneacetone)dipalladium (0), tris(tribenzylidene acetylacetone)tripalladium (0), palladium acetate, palladium propionate, palladium butyrate, palladium benzoate, palladium acetylacetonate, palladium nitrate, palladium sulfate, palladium chloride, platinous acetate and platinum acetylacetonate. When inorganic strong acid salts of platinum-group metals are used, it is desirable to cause a base such as potassium acetate, sodium alcoholate or a tertiary amine to be present together. Of the platinum-group metals, palladium is preferred in view of its reactivity. It is particularly preferred to use 0-valent olefin complexes or divalent organic compounds.

The monodentate ligand (b) used as the catalyst ingredient is an electron donating compound having an element of Group V of the periodic table, i.e. nitrogen, phosphorus, arsenic or antimony, as a coordinating atom. Specific examples include nitrogen-containing compounds such as pyridine, quinoline, trimethylamine, triethylamine and tributylamine; phosphorus-containing compounds such as triethyl phosphine, tri-n-butyl phosphine, tri-n-dodecyl phosphine, triphenyl phosphine, tri-o-tolyl phosphine, tri-p-biphenyl phosphine, tri-o-methoxyphenyl phosphine, phenyldiphenoxy phosphine, triethyl phosphite, tri-n-butyl phosphite, tri-n-hexyl phosphite, triphenyl phosphite, tri-o-tolyl phosphite and triphenyl thiophosphite; arsenic-containing compounds such as triethyl arsenic, tributyl arsenic and triphenyl arsenic; and antimony-containing compounds such as tripropyl antimony and triphenyl antimony. Of these, the nitrogen-containing compounds and phosphorus-containing compounds are preferred in respect of the activity, selectivity and economy of the reaction.

The monodentate ligand is not essential as a catalyst ingredient. But its use in a suitable amount can greatly increase the stability of the catalyst and reduce the amount of the catalyst used. If its amount becomes excessively large, the known allylic reaction becomes a main reaction. The amount of the monodentate ligand (b) should therefore be limited to not more than 2.5 moles, preferably 0.1 to 2 moles, especially preferably 0.3 to 1.8 moles, per mole of the metal compound.

The amount of the catalyst used in this invention may be properly chosen. Usually, the platinum-group metal compound (a) is used in a proportion of 0.01 to 10 moles, preferably 0.1 to 5 moles, per 100 moles of the starting compound [I]. The platinum-group metal compound (a) may be pre-reacted with the ligand (b). Usually, these ingredients are contacted in the reaction system to prepare the catalyst in situ.

The reaction of this invention proceeds in accordance with the following reaction scheme by contacting the starting material with the catalyst.

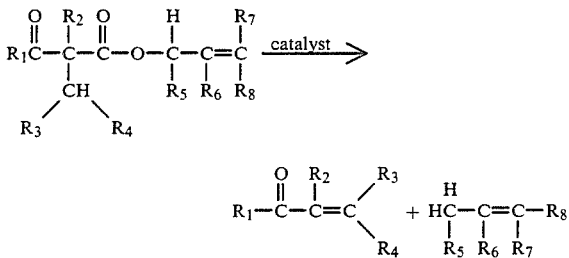

In carrying out the reaction, an allylic compound may be present in the reaction system, and this leads to a further improvement in the activity and stability of the catalyst. The allylic compound is an ester or ether having at least one allylic radical in the molecule. Specific examples include allyl acetate, methallyl acetate, crotyl acetate, 2-pentenyl acetate, cinnamyl acetate, allyl propionate, allyl butyrate, allyl benzoate, diallyl carbonate, diallyl oxalate, diallyl malonate, diallyl succinate, diallyl adipate, diallyl phthalate, methyl allyl ether, methyl methallyl ether, methyl crotyl ether, ethyl allyl ether, propyl allyl ether, butyl allyl ether, diallyl ether and phenyl allyl ether. Those having not more than 10 carbon atoms are preferred.

The amount of the allylic compound used may be selected properly. It is usually at least 0.5 mole, preferably 0.7 to 2.0 moles, per mole of the platinum-group metal compound.

There is no particular limitation on the method of adding the allylic compound. It may be added, for example, during the step of preparing the catalyst, or at the start of the reaction, or during the progress of the reaction. As required, it may be added in two or more portions at different times. Preferably, the allylic compound is added in the step of preparing the catalyst.

The reaction may be carried out in the presence of a diluent. Examples of the diluent are nitriles such as acetonitrile, propionitrile, butyronitrile and benzonitrile; amides such as dimethylformamide, diethylformamide, dimethylacetamide, dimethylpropionamide and N-methylpyrrolidone; ethers such as tetrahydrofuran, dioxane, dibutyl ether and ethylene glycol dimethyl ether; ketones such as acetone, methyl ethyl ketone and methyl isobutyl ketone cyclohexanone; esters such as methyl acetate, ethyl acetate, propyl acetate and ethyl propionate; alcohols such as ethanol, propanol, tert-butanol, ethylene glycol and diethylene glycol monoethyl ether; sulfoxides such as dimethyl sulfoxide and diethyl sulfoxide; and hydrocarbons such as n-hexane, cyclohexane, benzene, toluene and xylene. Of these, aprotic polar solvents, especially nitriles, amides, ethers, ketones and esters, are preferred.

The diluent is used normally in such a proportion that the concentration of the starting material in it becomes 1 to 50% by weight. The use of the diluent can increase the activity and selectivity of the reaction and the stability of the catalyst.

Other reaction conditions may be properly chosen. The reaction temperature is usually at least 20° C., preferably 50° to 150° C., and the reaction time is usually 5 minutes to 10 hours.

After the reaction, the desired product is separated from the reaction mixture in a customary manner to give the alpha,beta-unsaturated ketone having a high purity. The unsaturated ketones are used as intermediates for synthesis of various useful compounds, especially perfumes and medicines. For example, by the Michael addition of dimethyl malonate to 2-(2-cis-pentenyl)-2-cyclopenten-1-one and subsequent decarboxylation, methyl jasmonate useful as a perfume can be easily synthesized.

According to this invention, easily available compounds can be used as the catalyst, and the desired alpha,beta-unsaturated ketones can be produced with higher activity and selectivity than the conventional methods. The present invention can also improve the stability of the catalyst in the reaction system.

The following examples illustrate the present invention more specifically.

The stability of the catalyst in these examples was determined by observing the state of precipitation of palladium in the reaction system and evaluating it on the scale of A, B, C, D and E as follows:

A: No precipitation occurs after the lapse of 12 hours from the end of the reaction.
E: Precipitation begins during the reaction.
B to D: Varying degrees of precipitation between A and E.

EXAMPLE 1

A vessel was charged with 1 mole of allyl 1-(2-pentynyl)-2-oxocyclopentanecarboxylate of the following formula

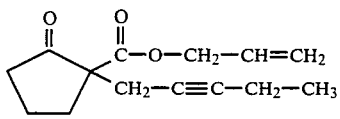

20 moles of acetonitrile and 0.01 mole of palladium acetate. At room temperature, they were rapidly stirred. The mixture was then heated to the boiling point of the solvent, and the reaction was carried out under reflux for 30 minutes. After the reaction, the reaction mixture was distilled under reduced pressure in a customary manner to give 2-(2-pentynyl)-2-cyclopenten-1-one (PCP for short) in a yield of 85%. This compound was identified by using its IR, NMR and mass spectra.

The state of the reaction system during the reaction and after the reaction was observed. Palladium began to be precipitated during the reaction, and after the end of the reaction, palladium precipitated more vigorously. Thus, the stability of the catalyst was evaluated as D.

EXAMPLE 2

Example 1 was repeated except that palladium acetylacetonate was used instead of palladium acetate. The yield of PCP was 80%. The state of precipitation of palladium was the same as in Example 1.

EXAMPLE 3

Example 1 was repeated except that tris(dibenzylidenediacetone)dipalladium (0) was used instead of palladium acetate. The yield of PCP was 83%. The state of precipitation of palladium was the same as in Example 1.

EXAMPLE 4

Example 1 was repeated except that a amount of triphenyl phosphine was used in addition to palladium acetate. The results are shown in Table 1. In either case, scarcely any precipitation of palladium during the reaction was observed. The stability of the catalyst was evaluated as C.

TABLE 1

| Run No. | Invention | | | | Control |
|---|---|---|---|---|---|
|  | 1 | 2 | 3 | 4 | 5 |
| Amount of triphenyl phosphine (moles) | 0.005 | 0.01 | 0.015 | 0.02 | 0.03 |
| Mole ratio of triphenyl phosphine to palladium | 0.5 | 1.0 | 1.5 | 2.0 | 3.0 |
| Yield of PCP (%) | 82 | 85 | 87 | 71 | 6 |

It is seen from the results obtained above that when the amount of triphenyl phosphine used is within a certain range, good results can be obtained in respect of the stability of the catalyst and the yield of the desired product.

EXAMPLE 5

Run No. 3 of Example 4 was repeated except that each of the ligands indicated in Table 2 was used instead of triphenyl phosphine. The results are shown in Table 2. The results show that a monodentate ligand is preferred to a bidentate ligand.

TABLE 2

| Run No. | Invention | | | | Control |
|---|---|---|---|---|---|
|  | 1 | 2 | 3 | 4 | 5(*2) |
| Ligand | Triphenyl phosphite | Pyridine | Triethylamine | Triphenyl arsenic | ADP(*1) |
| Yield of PCP (%) | 81 | 82 | 77 | 75 | 60 |

(*1)alpha,beta-ethylenedi(diphenyl)phosphine
(*2)The amount of ADP was 0.01 mole.

EXAMPLE 6

Run No. 3 of Example 4 was repeated except that 20 moles of each of the solvents indicated in Table 3 was used instead of acetonitrile. The results are also shown in Table 3.

TABLE 3

| Run No. | Solvent | Yield of PCP (%) |
|---|---|---|
| 1 | Propionitrile | 85 |
| 2 | Benzonitrile | 87 |
| 3 | Dimethylformamide | 87 |
| 4 | Dioxane | 83 |
| 5 | t-Butanol | 74 |
| 6 | Toluene | 76 |

EXAMPLE 7

Run No. 3 of Example 4 was repeated except that each of the compounds indicated in Table 4 was used as a starting material. The results are shown in Table 4.

TABLE 4

| Run No. | Starting material | Product | Yield (mole %) |
|---|---|---|---|
| 1 | cyclohexanone with C(=O)-O-CH₂-CH=CH₂ and CH₃ substituents at 2-position | 2-methyl-2-cyclohexen-1-one | 92 |
| 2 | cyclohexanone with C(=O)-O-CH₂-CH=CH₂ and CH₂-CH₂-C(=O)-O-CH₃ substituents at 2-position | 2-cyclohexen-1-one with CH₂-CH₂-C(=O)-O-CH₃ substituent | 95 |

TABLE 4-continued

| Run No. | Starting material | Product | Yield (mole %) |
|---|---|---|---|
| 3 | 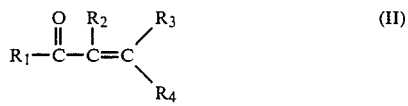 | H₃C—C(=O)—C(CH₃)=CH—CH₃ | 75 |

EXAMPLE 8

A vessel was charged with 1 mole of allyl 1-(2-pentynyl)-2-oxocyclopentanecarboxylate, 20 moles of acetonitrile, 0.003 mole of palladium acetate, 0.0045 mole of triphenyl phosphine and 0.003 mole of diallyl carbonate. They were rapidly stirred at room temperature, and the mixture was heated to the boiling point of the solvent. The reaction was carried out under reflux until the conversion of the starting material became nearly 100%. Since the reaction ended in about 3 hours, the product was distilled under reduced pressure in a customary manner. PCP was obtained in a yield of 88%. The stability of the catalyst was evaluated as A.

EXAMPLE 9

Example 8 was repeated until the conversion of the starting material became nearly 100% except that each of the allyl compounds indicated in Table 5 was used instead of diallyl carbonate. The results are shown in Table 5.

TABLE 5

| Run No. | Invention | | | |
|---|---|---|---|---|
|  | 1 | 2 | 3 | 4 |
| Allyl compound | — | Diallyl adipate | Allyl acetate | Phenyl allyl ether |
| Yield of PCP (%) | 85 | 85 | 85 | 80 |
| Reaction time (hr) | 10 | 5 | 5 | 5 |
| Stability of the catalyst | C | B | B | B |

EXAMPLE 10

A vessel was charged with 1 mole of allyl 1-(2-pentynyl)-2-oxocyclopentanecarboxylate, 20 moles of acetonitrile, 0.01 mole of palladium acetate, 0.015 mole of triphenyl phosphite and 0.01 mole of allyl acetate, and they were rapidly stirred at room temperature. The mixture was heated to the boiling point of the solvent, and under reflux, the reaction was carried out for 30 minutes. PCP was obtained in a yield of 82%. The stability of the catalyst was evaluated as B.

EXAMPLE 11

Example 10 was repeated except that pyridine was used instead of triphenyl phosphite. The yield of PCP was 82%, and the stability of the catalyst was evaluated as B.

EXAMPLE 12

Example 8 was repeated except that palladium acetylacetonate was used instead of palladium acetate. Nearly the same results as in Example 8 were obtained.

EXAMPLE 13

Example 8 was repeated except that tris(dibenzylideneacetone)dipalladium was used instead of palladium acetate. Nearly the same results as in Example 8 were obtained.

What we claim is:

1. A process for producing alpha,beta-unsaturated ketones represented by the following general formula

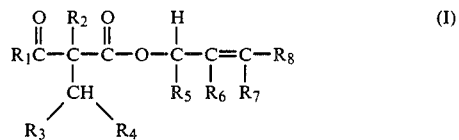

wherein $R_1$ represents an alkyl or alkylene group, $R_2$ represents an alkyl, alkenyl, alkynyl, alkylene, alkoxycarbonyl, alkeneoxycarbonyl, alkoxyalkyl or alkoxycarbonylalkyl group, $R_3$ and $R_4$ represent a hydrogen atom or an alkyl or alkylene group, and $R_1$, $R_2$, $R_3$ and $R_4$ may be linear or form a ring when taken together in arbitrary combinations, which comprises contacting an alpha-disubstituted-beta-keto acid ester represented by the general formula $$R_1\overset{O}{\underset{}{C}}-\underset{\underset{R_3}{\overset{CH}{\diagdown}R_4}}{\overset{R_2}{\underset{}{C}}}-\overset{O}{\underset{}{C}}-O-\overset{H}{\underset{R_5}{C}}-\underset{R_6}{C}=\underset{R_7}{C}-R_8 \qquad (I)$$

wherein $R_1$, $R_2$, $R_3$ and $R_4$ are as defined, and $R_5$, $R_6$, $R_7$ and $R_8$ represents a hydrogen atom or an alkyl group, said alpha-disubstituted-beta-keto acid ester being an ester formed between a keto acid having not more than 20 carbon atoms and an allylic alcohol having not more than 6 carbon atoms, with a catalyst consisting essentially of (a) a palladium compound or (b) a mixture of a palladium compound and monodentate ligand selected from the group consisting of N-containing compounds, P-containing compounds and As-containing compounds, said mixture being composed of 1 mole of the palladium compound and not more than 2.5 moles of the monodentate ligand.

2. The process of claim 1 wherein the amount of the palladium metal compound (a) is 0.01 to 10 moles per 100 moles of the alpha-disubstituted-beta-keto acid ester of formula [I].

3. The process of claim 1 wherein the catalyst is composed of 1 mole of the palladium metal compound (a) and 0.1 to 2 moles of the monodentate ligand (b).

4. The process of claim 1 wherein the monodentate ligand (b) is a nitrogen- or phosphorus-containing compound.

5. The process of claim 1 wherein the monodendate ligand (b) is a phosphine, phosphite or tertiary amine.

6. The process of claim 1 wherein the palladium compound is a compound of Pd (0) or an organic compound of Pd (II).

7. The process of claim 1 wherein the reaction is carried out in the presence of a diluent.

8. The process of claim 7 wherein the diluent is an aprotic polar solvent.

9. The process of claim 1 wherein the reaction is carried out in the presence of an allyl compound.

10. The process of claim 9 wherein the allyl compound is an allylic ester or allylic ether having not more than 10 carbon toms.

11. The process of claim 10 wherein the keto acid is a 1-substituted-2-oxocycloalkanecarboxylic acid.

12. The process of claim 11 wherein the cycloalkane moiety has 5 to 12 carbon atoms.

13. The process of claim 11 wherein the substituent is an unsaturated hydrocarbon radical.

14. The process of claim 1 wherein the alpha-disubstituted-beta-keto acid ester [I] is contacted with the catalyst at a temperature of at least 20° C. for a period of 5 minutes to 10 hours.

15. The process of claim 1 wherein the alpha-disubstituted-beta-keto acid ester of the formula [I] is an ester formed between an alpha-disubstituted-beta-keto acid selected from the group consisting of 1-alkyl-2-oxocyclopentanecarboxylic acids, 1-alkenyl-2-oxocyclopentanecarboxylic acids, 1-alkynyl-2-oxocyclopentanecarboxylic acids, 1-alkyl-2-oxocyclohexanecarboxylic acids, 1-alkenyl-2-oxocyclohexanecarboxylic acids, 1-alkoxycarbonylalkyl-2-oxocyclohexanecarboxylic acids, 1-alkenoxycarbonyl-2-oxocyclohexanecarboxylic acids, 1-alkoxyalkyl-2-oxocyclohexanecarboxylic acids, 1-alkyl-2-oxocyclododecanecarboxylic acid, 1-acetyl-1-cyclopentanecarboxylic acid, alpha-dialkylacetoacetic acids, and alpha-dialkyl-beta-oxononanoic acid, and an allylic alcohol selected from the group consisting of allyl alcohol, methallyl alcohol, crotyl alcohol, 2-pentenyl alcohol and 2-ethyl-2-butenol.

16. The process of claim 6 wherein the palladium compound is tris(dibenzylideneacetone)dipalladium (0), tris(tribenzylideneacetylacetone)tripalladium (0), palladium acetate, palladium propionate, palladium butyrate, palladium benzoate, palladium acetylacetonate, palladium nitrite, palladium sulfate, or palladium chloride.

17. The process of claim 1 wherein the catalyst is the mixture of the palladium compound and the monodentate ligand.

18. The process of claim 17 wherein the monodentate ligand is selected from the group consisting of pyridine, quinoline, trimethylamine, triethylamine, tributylamine, triethylphosphine, tri-n-butyl phospine, tri-n-dodecyl phosphine, triphenyl phosphine, tri-o-tolyl phosphine, tri-p-biphenyl phosphine, tri-o-methoxyphenyl phosphine, phenyldiphenoxy phosphine, triethyl phosphite, tri-n-butyl phosphite, tri-n-hexyl phosphite, triphenyl phosphite, tri-o-tolyl phosphite, triphenyl thiophosphite, triethyl arsenic, tributyl arsenic and triphenyl arsenic.

19. The process of claim 1 wherein the amount of the palladium compound is 0.1 to 5 moles, per 100 moles of the alpha-disubstituted-beta-keto acid ester of formula [I].

20. The process of claim 10 wherein the allyl compound is allyl acetate, methallyl acetate, crotyl acetate, 2-pentenyl acetate, cinnamyl acetate, allyl propionate, allyl butyrate, allyl benzoate, diallyl carbonate, diallyl oxalate, diallyl malonate, diallyl succinate, diallyl adipate, diallyl phthalate, methyl allyl ether, methyl methallyl ether, methyl crotyl ether, ethyl allyl ether, propyl allyl ether, butyl allyl ether, diallyl ether and phenyl allyl ether.

21. The process of claim 10 wherein the amount of the allyl compound is from 0.7 to 2.0 moles, per mole of the palladium compound.

* * * * *

UNITED STATES PATENT AND TRADEMARK OFFICE
CERTIFICATE OF CORRECTION

PATENT NO. : 4,575,570
DATED : March 11, 1986
INVENTOR(S) : HIDEAKI KATAOKA, ET AL It is certified that error appears in the above-identified patent and that said Letters Patent is hereby corrected as shown below:

Claim 11, line 1, (column 9, line 8)
   delete "claim 10", insert --claim 1--.

Signed and Sealed this

Twenty-ninth Day of July 1986

[SEAL]

Attest:

DONALD J. QUIGG

Attesting Officer

Commissioner of Patents and Trademarks